US008426165B2

(12) United States Patent
Cho et al.

(10) Patent No.: US 8,426,165 B2
(45) Date of Patent: Apr. 23, 2013

(54) PROCESS FOR PRODUCING FERMENTATION PRODUCT FROM CARBON SOURCES CONTAINING GLYCEROL USING CORYNEBACTERIA

(75) Inventors: Kwang-myung Cho, Gyeonggi-do (KR); Kyung-oh Choi, Seoul (KR); Hyun-ae Bae, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 673 days.

(21) Appl. No.: 12/522,304

(22) PCT Filed: Jan. 22, 2008

(86) PCT No.: PCT/KR2008/000391
§ 371 (c)(1),
(2), (4) Date: Jul. 7, 2009

(87) PCT Pub. No.: WO2008/091093
PCT Pub. Date: Jul. 31, 2008

(65) Prior Publication Data
US 2010/0129884 A1    May 27, 2010

(30) Foreign Application Priority Data
Jan. 24, 2007    (KR) .................. 10-2007-0007513

(51) Int. Cl.
*C12N 15/00*    (2006.01)
(52) U.S. Cl.
USPC ........................... 435/69.1; 435/41; 435/170
(58) Field of Classification Search .................. None
See application file for complete search history.

(56) References Cited

U.S. PATENT DOCUMENTS

| | | | |
|---|---|---|---|
| 5,457,040 A | 10/1995 | Jarry et al. | |
| 5,633,154 A | 5/1997 | Schaefer et al. | |
| 5,804,414 A | 9/1998 | Moriya | |
| 6,200,785 B1 | 3/2001 | Kreutzer et al. | |
| 6,221,636 B1 | 4/2001 | Hayakawa et al. | |
| 6,740,742 B2 | 5/2004 | Mackel et al. | |
| 6,746,855 B2 | 6/2004 | Kreutzer et al. | |
| 6,861,246 B2 | 3/2005 | Kreutzer et al. | |
| 6,872,553 B2 | 3/2005 | Eikmanns et al. | |
| 6,913,909 B2 | 7/2005 | Ziegler et al. | |
| 6,962,989 B1 | 11/2005 | Pompejus et al. | |
| 7,160,711 B2 | 1/2007 | Bathe et al. | |
| 8,048,650 B2 | 11/2011 | Koo et al. | |
| 8,058,036 B2 | 11/2011 | Koo et al. | |
| 2002/0055153 A1 | 5/2002 | Kreutzer et al. | |
| 2002/0192674 A1 | 12/2002 | Hermann et al. | |
| 2002/0197605 A1 | 12/2002 | Nakagawa et al. | |
| 2003/0055232 A1 | 3/2003 | Li et al. | |
| 2005/0153402 A1 | 7/2005 | Pompejus et al. | |
| 2005/0255568 A1 | 11/2005 | Bailey et al. | |
| 2006/0084152 A1 | 4/2006 | Pompejus et al. | |
| 2008/0293100 A1* | 11/2008 | Wendisch et al. ............ 435/69.1 | |
| 2010/0015673 A1 | 1/2010 | Koo et al. | |
| 2010/0028957 A1 | 2/2010 | Koo et al. | |
| 2010/0143984 A1 | 6/2010 | Park et al. | |
| 2010/0330624 A1 | 12/2010 | Jang | |

FOREIGN PATENT DOCUMENTS

| | | |
|---|---|---|
| CN | 1187540 A | 7/1998 |
| DE | 101 10 760 A1 | 8/2001 |
| EP | 0733710 A1 | 9/1996 |
| EP | 0854189 A2 | 7/1998 |
| EP | 1715055 A | 10/2006 |
| JP | 2-079788 A | 4/1987 |
| JP | Hei 7-121228 | 12/1995 |
| JP | 09-070291 | 3/1997 |
| JP | 10-215883 A | 8/1998 |
| JP | 2001-037495 A | 2/2001 |
| JP | 2002-508921 A | 3/2002 |
| JP | 2003-503006 A | 1/2003 |
| JP | 2006-512922 | 4/2006 |
| KR | 10-0313134 | 10/2001 |
| KR | 1020050065712 | 6/2005 |
| KR | 1020050065712 A | 6/2005 |
| KR | 1020060068505 A | 6/2006 |
| KR | 10-2008-025355 A | 3/2008 |
| WO | WO 92/02627 | 2/1992 |
| WO | WO 2002/053707 | 7/2002 |
| WO | WO 2005/121349 | 12/2005 |
| WO | WO 2005/121349 A2 | 12/2005 |
| WO | WO 2006/065095 A1 | 6/2006 |
| WO | WO 2006/071099 A1 | 7/2006 |
| WO | WO 2007/039532 | 4/2007 |
| WO | WO 2008/033001 | 3/2008 |

OTHER PUBLICATIONS

Cerdeno-Tarraga et al., Nucleic Acids Research, vol. 31(22), pp. 6516-6523, Nov. 2003.*
Ngo et al. in The Protein Folding Problem and Tertiary Structure Prediction, 1994, Merz et al. (ed.), Birkhauser, Boston, MA, pp. 433 and 492-495.*
Office Action issued Jul. 6, 2011 in U.S. Appl. No. 12/518,572.
Office action issued Jul. 11, 2011 in U.S. Appl. No. 12/518,578.
Beijer et al. (Feb. 1993) Journal of General Microbiology, 139(2):349-359, "The *glpP* and *glpF* genes of the glycerol regulon in *Bacillus subtilis*".
Biebl (1998) Appl Microbiol Biotechnol. 50:24-29, "Fermentation of glycerol to 1,3-propanediol and 2,3-butanediol by *Klebsiella pneumonia*".
Doleyres et al. (2005) Appl Microbiol Biotechnol. 68:467-474, "Production of 3-hydroxypropionaldehyde using a two-step process with *Lactobacillus reuteri*".

(Continued)

*Primary Examiner* — Richard Hutson
(74) *Attorney, Agent, or Firm* — Swanson & Bratschun, L.L.C.

(57) ABSTRACT

The present invention relates to a method for producing fermentation product from various carbon sources containing glycerol using Corynebacteria. More particularly, the present invention relates to a method for producing fermentation product from carbon sources containing glycerol or a part of glycerol with high yield and high productivity, by fermenting Corynebacteria introduced with the foreign gene glpDFK facilitating the use of glycerol and accumulating industrially useful amino acids in the culture medium.

6 Claims, 2 Drawing Sheets

OTHER PUBLICATIONS

González-Pajuelo et al. (2004) J Ind Microbiol Biotechnol. 31:442-446, "Production of 1,3-propanediol by *Clostridium butyricum* VPI 3266 using a synthetic medium and raw glycerol".
Heller et al. (Oct. 1980) Journal of Bacteriology 144(1):274-278, "Substrate Specificity and Transport Properties of the Glycerol Facilitator of *Escherichia coli*".
Himmi et al. (2000) Appl Microbiol Biotechnol 53:435-440, "Propionic acid fermentation of glycerol and glucose by *Propionbacterium acidipropionici* and *Propionibacterium freudenreichii* ssp. *shennanii*".
Ito et al. (2005) Journal of Bioscience and Bioengineering 100(3):260-265, "Hydrogen and Ethanol Production from Glycerol-Containing Wastes Discharged after Biodiesel Manufacturing Process".
Kawaguchi et al. (May 2006) Applied and Environmental Microbiology 72(5):3418-3428, "Engineering of a Xylose Metabolic Pathway in *Corynebacterium glutamicum*".
Lin et al. (1976) Ann. Rev. Microbiol. 30:535-578, "Glycerol Dissimilation and its Regulation in Bacteria".
Menzel (1997) Enzyme and Microbial Technology 20:82-86, "High Concentration and Productivity of 1,3-propanediol from continuous fermentation of glycerol by *Klebsiella pneumoniae*".
Parche et al. (Jul. 2001) J. Mol. Microbiol. Biotechnol. 3(3):415-422, "*Corynebacterium diphtheriae*: a PTS View to the Genome".
Paulsen et al. (Oct. 2000) Microbiology146:2343-2344, "Functional genomic studies of dihydroxyacetone utilization in *Escherichia coli*".
Talarico et al. (Dec. 1988) Antimicrobial Agents and Chemotherapy 32(12):1854-1858, "Production and Isolation of Reuterin, a Growth Inhibitor Produced by *Lactobacillus reuteri*".
Voegele (Feb. 1993) Journal of Bacteriology, 175(4):1087-1094, "Glycerol Kinase of *Escherichia coli* Is Activated by Interaction with the Glycerol Facilitator".
Wang et al. (2001) Biotechnology Advances 19:201-223, "Glycerol production by microbial fermentation: A review".
U.S. Appl. No. 12/867,649, filed Sep. 13, 2010, Jang et al.
International Search Report issued May 16, 2008 in PCT/KR2008/000391.
Written Opinion issued May 16, 2008 in PCT/KR2008/000391.
Hayashi (2006) Appl. Microbiol. Biotechnol. 72:783-789, "A *leu* mutation leading to increased L-lysine production and *rel*-independent global expression changes in *Corynebacterium glutamicum*".
Tangney (2000) Journal of Molecular Microbiology and Biotechnology 2(1):71-80, "Analysis of a catabolic operon for sucrose transport and metabolish in Clostridium acetobutylicum ATCC 824" (Abstract only).
Liebl, W. "International Journal of Systematic Bacteriology, 1991, vol. 41, pp. 255-260, Transfer of *Brevibacterium divaricatum* DSM 20297T, "*Brevibacterium flavum*" DSM 20411, "*Brevibacterium lactofermenturn*" DSM 20412 and DSM 1412, and Corynebacteriumlilium DSM 20137T to *Corynebacteriurn glutamicum* and Their Distinction by rRNA Gene Restriction Patterns".
Vertes, A.A. Mol.Gen.Genet.,1994,vol. 245, pp. 397-405, "Transposon Mutagenesis of Coryneform Bacteria".
Accession AXBX248360, Nov. 2006.
Beijer et al. (1992) FEMS Microbiology Letters 100:217-220, "Utilisation of glycerol and glycerol 3-phosphate is differently affected by the• phosphotransferase system in *Bacillus subtilis*".
Mormann (Aug. 10, 2006) BMC Genomics, 7:205, doi:10.1186/1471-2164-205, "Random mutagenesis in *Corynebacterium glutamicum* ATCC 13032 using an IS6100-based transposon vector identified the last unknown gene in the histidine biosynthesis pathway".
Nishise et al. (1985) Agri. Biol. Chem. 49(3):629-636, "Glycerol Dehydrogenase and Glycerol Dissimilation in *Cellulomonas* sp. NT3060".
Peters-Wendisch et al. (Nov. 2005) Applied and Environmental Microbiology, 71(11):7139-7144, "Metabolic Engineering of *Corynebacterium glutamicum* for L-Serine Production".
Written Opinion (English translation) issued in PCT/KR2009/001845 mailed Nov. 27, 2009.
Database UnitProt [Online] Jul. 5, 2004, "SubName: Full=Putative uncharacterized protein".
Eggeling (1994) Amino Acids 6:261-272, "Biology of L-lysine overproduction by *Corynebacterium glutamicum*".
European Search Report issued Dec. 30, 2009 in EP 07860725.6 (PCT/KR2007/006935).
Hayes, Finbarr (2003) Annu. Rev. Genet. 37:3-29, "Transposon-Based Strategies for Microbial Functional Genomics and Proteomics".
Ikeda et al. (Aug. 2003) App. Microbiol. and Biotechnol. 62( 2-3, 1): 99-109, "The *Corynebacterium glutamicum* genome: Features and impacts on biotechnological processes".
International Preliminary Report on Patentability issued Oct. 12, 2010 and Written Opinion for PCT/KR2009/001845.
International Search Report issued in PCT/KR2009/001845 mailed Nov. 27, 2009.
Mitsuhashi et al. (Nov. 2006) Biosci., Biotechnol., and Biochem. 70(11): 2803-2806, "Disruption of malate:quinone oxidoreductase increases L-lysine production by *Corynebacterium glutamicum*".
Tsuge et al. (2005) Microbiology 151:501-508, "A New Insertion Sequence, ISI4999, from *Corynebacterium glutamicum*".
Tzvetkov et al. (Jul. 2003) Microbiology 149(7):1659-1673, "Genetic dissection of trehalose biosynthesis in *Corynebacterium glutamicum*: Inactivation of trehalose production leads to impaired growth and altered cell wall lipid composition".
Office Action issued Jan. 12, 2011 in U.S. Appl. No. 12/518,578.
Office Action issued Jan. 7, 2011 in U.S. Appl. No. 12/518,572.
Accession AX 121271, May 11, 2001.
Contador C.A. et al., "Ensemble modeling for strain development of l-lysine-producing *Escherichia coli*," Metabolic Engineering, Jul. 1, 2009, pp. 221-233, vol. 11, No. 4-5, Academic Press.
Extended European Search Report dated Jan. 5, 2010, for European Patent Application No. 07808268.
GenBank Accession No. BA000036 (Oct. 2004).
Koffas Mattheos A.G. et al., "Effect of pyruvate carboxylase overexpression on the physiology of *Corynebacterium glutamicum*," Applied and Environmental Microbiology, Nov. 2002, pp. 5422-5428, vol. 68, No. 11.
Yamada (Apr. 1973) Applied Microbiology 24(4) 636-640, "Production of D-alanine by *Cornebacterium facians*".
International Search Report dated Jan. 2, 2008, for PCT International Patent Application No. PCT/KR2007/004478.
Moon, et al. (2005) FEMS Microbiology Letters, "Analyses of enzyme II gene mutants for sugar transport and heterologous express of fructokinase gene in *Corynebacterium glutamicum* ATCC 13032," vo. 244, p. 259-266.

\* cited by examiner

SEQUENCE LISTING

```
<160> NUMBER OF SEQ ID NOS: 10

<210> SEQ ID NO 1
<211> LENGTH: 29
<212> TYPE: DNA
<213> ORGANISM: Artificial Sequence
<220> FEATURE:
<223> OTHER INFORMATION: primer 1

<400> SEQUENCE: 1
gatgcggccg cgctgtgtgg cgtatgtcg                                29

<210> SEQ ID NO 2
<211> LENGTH: 31
<212> TYPE: DNA
<213> ORGANISM: Artificial Sequence
<220> FEATURE:
<223> OTHER INFORMATION: primer 2

<400> SEQUENCE: 2
gatgcggccg caatcatcaa acccaacccc a                             31

<210> SEQ ID NO 3
<211> LENGTH: 4261
<212> TYPE: DNA
<213> ORGANISM: Artificial Sequence
<220> FEATURE:
<223> OTHER INFORMATION: DNA sequence of glpDFK-1 from pECCG117-cdi
      glpDFK-1

<400> SEQUENCE: 3
gctgtgtggc gtatgtcgcg cagcccgttt tttgccgcca ccaccactgg ttacatcacc      60
tgctaccagt tgttatcatc tccgaaacta aaaaacttgc tctaggggtc tagtctgcct     120
aacttacggt tcagtagggt tggggcaaac ctcggacgca agaaggagt gtggcaacta      180 tgaccacgaa atcccattgc acattcaacc ccgactacta ccaggacgtc tggcagcgct     240
```

-continued

```
tcggtgaaga agaatacgac gttgtcgtca tcggtggcgg ctccgtcggc gcaggcgcag    300
gcctcgacgc agccatccgc ggcctcaaag tggccgtcgt agagtcccga gacttcgcag    360
ccggcacctc ctcacgatca tcaaaaatgt tccacggtgg cctgcgatat ctcgccatgc    420
tggacttcaa gctagtggcc gaatccctcc acgagcgcga actcaacatg tcgacgctcg    480
caccgcacct agtcaagccg ctgaaattcc tcttcccct cacacaccac gtgtgggaac    540
gggtgatgat gttcggcggc tttactcttt acgacctcat gggcggcgca aaatcagtcc    600
ccatgcaaaa gcactactcc cgcaagggaa cactcgccat ggccccagga ctaaaagacg    660
acgctgtggt cggatccgtc cgctactttg acacgcttgt cgacgacgcc cgccacacca    720
tgacagtcct acgcaccgcc ggcgaactcg gcgcagatgt tcgcccctcc acccaagtag    780
tcggctttga aaagacggc caacgcgtgg tcggcgccat cctccaagac accgacaccg    840
gcgaacaaac caccatccgc ggcaaggtat tcatcaacgc caccggcgta tggaacgacc    900
acattgaaaa gctcgccggc ggcaacggcc ccttctcggt ccacgcctcc aagggcgtac    960
acatcgtggt accaaagaac gtctttgatg ccgacgcagc catgtgcttt gtcaccgaaa    1020
agtccgtgct cttcgtgatc ccatggggtg aatactggat catcggcacc accgacaccg    1080
actgggatct caaccgcgca gaccccgcac caactgccgc cgacatcaac tacatcctcg    1140
acgaagtcaa ccagcgagtc cgccggccca tccaacactc cgacatcgtc ggcgtgtact    1200
ccggactccg cccgctgctc tccggcaaat ccgacaccac caccaagctg tcgcgcaacc    1260
acgccgtagc aaaggtcatg cctggactcg tctccgtcgc cggcggtaag tacaccacct    1320
accgtgtgat cggcaaggat gcagtcgacc tcgccaccga agacttggac ttccgcgtac    1380
cagcctccga atcggaacgc accccgatcc tcggtgccga cggctaccac gccctacaaa    1440
accaagcacc acgcatcgcc cgcaccttcg gcaccacaga ggacgtcgtc gagcacctgc    1500
tcggccgcta cggctccctc gtccatgagg tcctagaacc gagcgtcgat aaacctgagc    1560
tgctcgaacc catcccaggc gcgccgggct acattaaggc agaggccgtc tatgccgtca    1620
cccacgaggg tgccctgcac gtcgaggaca tcgtggaacg tcgcctacgt gccggcatcg    1680
aatacgccga ccgtggcgtt gccgcagctc ccgccatcgc cgagctcgtt gccgactacc    1740
ttggctggga cgccgagcgc accgccgccg aggtcaccgc gttcaccgac cgcgtgtccg    1800
ccgaaatcgc cgccgagaag gagctcactg acaaagccgc caacgagcac atcgtggcag    1860
gctccgcggt gcgcagctat gtggatgtgt caggtgataa ctaatgaccg ccctacaagc    1920
attcggctgg gagttttttgg gcacagccct cctgcttctc ctcggtaacg gcgtttgcgc    1980
cgtcaacagc ctgcgcacct ccgcaggcaa aggcactggc tgggtgctta tcgctttcgg    2040
ctggggcatg gcggtattcg tcggtgcctc agtggcaagc cccagcggcg gccacctcaa    2100
cccagcggtc actatcgcgc tggcgatcaa aggcagcaca ccatggaacc tggtaggcgg    2160
ctatgttctc gggcagttcc tcggagccat gtttggtgca atcctgtgct ggctgacatt    2220
caagcagctt ttcgacgcca acaacaccga cgaaaacgga aacgtcacgg agctaaccg    2280 caccaccggc ggtatcttct tcaccggccc cgcccacaat cagaacgggt ggaacatggt    2340
caccgagttc atcggcacct gcgtactgct gctgttcatc ttcttcggcc ccacggcgg    2400 cgacctaggc cccatgacct atttcgcagt cgcctttgtg atcgttgcca taggcttgtc    2460
gctaggcaca ccgaccggct acgccatcaa ccctgtgcgt gacctcggcc ccgcctgat    2520 gtacgccttc gtgctgccca ttaaagacaa aggatccgcg aactgggcct atgcctgggt    2580
tccgatcgtc ggccccatga tcgccgcggt cttctgcgga gtgctggcca ctgtagtgct    2640
```

-continued

```
gtagtgaaag ggaaccacac caatgaatca accacagtat gttgctgcga ttgaccaagg   2700
aacgacgtcg acacgctgca tcattttcga ccacaacggc caacaagtag gcgttggcca   2760
gtacgaacac gaacaaatct tcccccaaaa aggctgggta gagcacaacc caatggaaat   2820
ctgggccagc acgcgccaag ccgttgggac agcactcgcc gaaagcgacg tctcccgtga   2880
agacatcgta gccgtaggca taacaaacca gcgtgaaacc acggtggtct ggaacaaaac   2940
tactggtgaa cccatatata cgccattgt gtggcaggac acccgcacta actccatctg    3000
ctcggagtta gcccaaggcg accctgcccg gtggcagaaa cgtaccggtt tgctcatcaa   3060 ctcataccc gcgggccccc gactcaagtg gatattggac aacgtcgagg gtgcccgcga    3120
actagcagag aacggcgatt tgctcttcgg aaccattgat acgtggttgc tgtgaaccct   3180
gaccggcggt gccgagggtg acaacggcca gcctgccgtt cacgctaccg acgtaaccaa   3240
tgcctcccgc accctactca tggatctgga atccctgcaa tgggatgagg aactatgtgc   3300
cgcgttggat attccaatgc aggtgttgcc agagattcgt ccttcagttg gtaacttcgg   3360
ccaagtacgt gcacgtggat cactagctgg tgttccgatc cgcgccatcc tcggtgacca   3420
gcaagccgca atgttcggac aggcatgctt ccggccaggt gatgccaaat gtacatacgg   3480
cacggggttg ttccttctgg agaacacagg caaaccccg aagcattccg aaaacggttt    3540
gctcaccacc gtgtgtttcc agctcgaagg cgaaaaaccg gtctatgccc tcgaaggatc   3600
cgttgccatg gggggctcgc tcgtccaatg gctacgcgac aaccttcaaa tcatcccgaa   3660
ctcgcccgcc attgaaaacc tcgcacgcga agtaccgac aacggtggcg tgtacatcgt    3720
ccccgcattc tccggactat tcgcaccacg ctggcgcccc gacgcccgcg gggtcatcgt   3780
gggcctgacc cgctttgcca accgcaagca cctcgcccgc gcagtactcg aggccaccgc   3840
ctaccaagtg cgcgaagtga tcgatgccat ggtcgcggat tccggagtag aactcaccga   3900
aatgcgtgtc gacggcggca tggtcatgaa cgaactgctc atgcaattcc aagccgacgt   3960
cctacgatcc gacgtcacgc gccccaagaa catcgagacc acagccaccg gcgtagccta   4020
cgcagccggc ctcggcgtgg gctactggga cagcctcgac gtactccgca acatgaacga   4080
agtggacaaa acctggcacg ccaagatgga cgccgacaag atcgacgagc tccttgccga   4140
atggaacaaa gcagtcgaac gcacctacaa ctgggaaaac taactgcctc ctgaaataac   4200
agcaaacccg acgaactatc cagctcgtcg ggtttgtttt gtggggttgg gtttgatgat   4260
t                                                                   4261
```

<210> SEQ ID NO 4
<211> LENGTH: 577
<212> TYPE: PRT
<213> ORGANISM: Artificial Sequence
<220> FEATURE:
<223> OTHER INFORMATION: Amino acid sequence of GlpD from pECCG117-cdi glpDFK-1

<400> SEQUENCE: 4

```
Met Ala Thr Met Thr Thr Lys Ser His Cys Thr Phe Asn Pro Asp Tyr
 1               5                  10                  15

Tyr Gln Asp Val Trp Gln Arg Phe Gly Glu Glu Glu Tyr Asp Val Val
                20                  25                  30

Val Ile Gly Gly Gly Ser Val Gly Ala Gly Ala Gly Leu Asp Ala Ala
            35                  40                  45

Ile Arg Gly Leu Lys Val Ala Val Val Glu Ser Arg Asp Phe Ala Ala
        50                  55                  60
```

```
Gly Thr Ser Ser Arg Ser Ser Lys Met Phe His Gly Leu Arg Tyr
 65                  70                  75                  80

Leu Ala Met Leu Asp Phe Lys Leu Val Ala Glu Ser Leu His Glu Arg
                 85                  90                  95

Glu Leu Asn Met Ser Thr Leu Ala Pro His Leu Val Lys Pro Leu Lys
            100                 105                 110

Phe Leu Phe Pro Leu Thr His His Val Trp Glu Arg Val Met Met Phe
        115                 120                 125

Gly Gly Phe Thr Leu Tyr Asp Leu Met Gly Gly Ala Lys Ser Val Pro
    130                 135                 140

Met Gln Lys His Tyr Ser Arg Lys Gly Thr Leu Ala Met Ala Pro Gly
145                 150                 155                 160

Leu Lys Asp Asp Ala Val Val Gly Ser Val Arg Tyr Phe Asp Thr Leu
                165                 170                 175

Val Asp Asp Ala Arg His Thr Met Thr Val Leu Arg Thr Ala Gly Glu
            180                 185                 190

Leu Gly Ala Asp Val Arg Pro Ser Thr Gln Val Val Gly Phe Glu Lys
        195                 200                 205

Asp Gly Gln Arg Val Val Gly Ala Ile Leu Gln Asp Thr Asp Thr Gly
    210                 215                 220

Glu Gln Thr Thr Ile Arg Gly Lys Val Phe Ile Asn Ala Thr Gly Val
225                 230                 235                 240

Trp Asn Asp His Ile Glu Lys Leu Ala Gly Gly Asn Gly Pro Phe Ser
                245                 250                 255

Val His Ala Ser Lys Gly Val His Ile Val Pro Lys Asn Val Phe
            260                 265                 270

Asp Ala Asp Ala Ala Met Cys Phe Val Thr Glu Lys Ser Val Leu Phe
        275                 280                 285

Val Ile Pro Trp Gly Glu Tyr Trp Ile Ile Gly Thr Thr Asp Thr Asp
    290                 295                 300

Trp Asp Leu Asn Arg Ala Asp Pro Ala Pro Thr Ala Ala Asp Ile Asn
305                 310                 315                 320

Tyr Ile Leu Asp Glu Val Asn Gln Arg Val Arg Arg Pro Ile Gln His
                325                 330                 335

Ser Asp Ile Val Gly Val Tyr Ser Gly Leu Arg Pro Leu Leu Ser Gly
            340                 345                 350

Lys Ser Asp Thr Thr Thr Lys Leu Ser Arg Asn His Ala Val Ala Lys
        355                 360                 365

Val Met Pro Gly Leu Val Ser Val Ala Gly Gly Lys Tyr Thr Thr Tyr
    370                 375                 380

Arg Val Ile Gly Lys Asp Ala Val Asp Leu Ala Thr Glu Asp Leu Asp
385                 390                 395                 400

Phe Arg Val Pro Ala Ser Glu Ser Glu Arg Thr Pro Ile Leu Gly Ala
                405                 410                 415

Asp Gly Tyr His Ala Leu Gln Asn Gln Ala Pro Arg Ile Ala Arg Thr
            420                 425                 430

Phe Gly Thr Thr Glu Asp Val Val Glu His Leu Leu Gly Arg Tyr Gly
        435                 440                 445

Ser Leu Val His Glu Val Leu Glu Pro Ser Val Asp Lys Pro Glu Leu
    450                 455                 460

Leu Glu Pro Ile Pro Gly Ala Pro Gly Tyr Ile Lys Ala Glu Ala Val
465                 470                 475                 480

Tyr Ala Val Thr His Glu Gly Ala Leu His Val Glu Asp Ile Val Glu
                485                 490                 495
```

```
Arg Arg Leu Arg Ala Gly Ile Glu Tyr Ala Asp Arg Gly Val Ala Ala
                500                 505                 510
Ala Pro Ala Ile Ala Glu Leu Val Ala Asp Tyr Leu Gly Trp Asp Ala
                515                 520                 525
Glu Arg Thr Ala Ala Glu Val Thr Ala Phe Thr Asp Arg Val Ser Ala
                530                 535                 540
Glu Ile Ala Ala Glu Lys Glu Leu Thr Asp Lys Ala Ala Asn Glu His
545                 550                 555                 560
Ile Val Ala Gly Ser Ala Val Arg Ser Tyr Val Asp Val Ser Gly Asp
                565                 570                 575

Asn

<210> SEQ ID NO 5
<211> LENGTH: 246
<212> TYPE: PRT
<213> ORGANISM: Artificial Sequence
<220> FEATURE:
<223> OTHER INFORMATION: Amino acid sequence of GlpF from pECCG117-cdi
      glpDFK-1

<400> SEQUENCE: 5

Met Thr Ala Leu Gln Ala Phe Gly Trp Glu Phe Leu Gly Thr Ala Leu
  1               5                  10                  15
Leu Leu Leu Leu Gly Asn Gly Val Cys Ala Val Asn Ser Leu Arg Thr
                 20                  25                  30
Ser Ala Gly Lys Gly Thr Gly Trp Val Leu Ile Ala Phe Gly Trp Gly
             35                  40                  45
Met Ala Val Phe Val Gly Ala Ser Val Ala Ser Pro Ser Gly Gly His
         50                  55                  60
Leu Asn Pro Ala Val Thr Ile Ala Leu Ala Ile Lys Gly Ser Thr Pro
 65                  70                  75                  80
Trp Asn Leu Val Gly Gly Tyr Val Leu Gly Gln Phe Leu Gly Ala Met
                 85                  90                  95
Phe Gly Ala Ile Leu Cys Trp Leu Thr Phe Lys Gln Leu Phe Asp Ala
                100                 105                 110
Asn Asn Thr Asp Glu Asn Gly Asn Val Thr Gly Ala Asn Arg Thr Thr
            115                 120                 125
Gly Gly Ile Phe Phe Thr Gly Pro Ala His Asn Gln Asn Gly Trp Asn
        130                 135                 140
Met Val Thr Glu Phe Ile Gly Thr Cys Val Leu Leu Leu Phe Ile Phe
145                 150                 155                 160
Phe Gly Pro Thr Gly Gly Asp Leu Gly Pro Met Thr Tyr Phe Ala Val
                165                 170                 175
Ala Phe Val Ile Val Ala Ile Gly Leu Ser Leu Gly Thr Pro Thr Gly
            180                 185                 190
Tyr Ala Ile Asn Pro Val Arg Asp Leu Gly Pro Arg Leu Met Tyr Ala
        195                 200                 205
Phe Val Leu Pro Ile Lys Asp Lys Gly Ser Ala Asn Trp Gly Tyr Ala
    210                 215                 220
Trp Val Pro Ile Val Gly Pro Met Ile Ala Ala Val Phe Cys Gly Val
225                 230                 235                 240
Leu Ala Thr Val Val Leu
                245

<210> SEQ ID NO 6
<211> LENGTH: 506
```

```
<212> TYPE: PRT
<213> ORGANISM: Artificial Sequence
<220> FEATURE:
<223> OTHER INFORMATION: Amino acid sequence of GlpK from pECCG117-cdi
      glpDFK-1

<400> SEQUENCE: 6
```

Met Asn Gln Pro Gln Tyr Val Ala Ala Ile Asp Gln Gly Thr Thr Ser
 1               5                  10                  15

Thr Arg Cys Ile Ile Phe Asp His Asn Gly Gln Gln Val Gly Val Gly
             20                  25                  30

Gln Tyr Glu His Glu Gln Ile Phe Pro Gln Lys Gly Trp Val Glu His
         35                  40                  45

Asn Pro Met Glu Ile Trp Ala Ser Thr Arg Gln Ala Val Gly Thr Ala
     50                  55                  60

Leu Ala Glu Ser Asp Val Ser Arg Glu Asp Ile Val Ala Val Gly Ile
 65                  70                  75                  80

Thr Asn Gln Arg Glu Thr Thr Val Val Trp Asn Lys Thr Thr Gly Glu
                 85                  90                  95

Pro Ile Tyr Asn Ala Ile Val Trp Gln Asp Thr Arg Thr Asn Ser Ile
            100                 105                 110

Cys Ser Glu Leu Ala Gln Gly Asp Pro Ala Arg Trp Gln Lys Arg Thr
        115                 120                 125

Gly Leu Leu Ile Asn Ser Tyr Pro Ala Gly Pro Arg Leu Lys Trp Ile
    130                 135                 140

Leu Asp Asn Val Glu Gly Ala Arg Glu Leu Ala Glu Asn Gly Asp Leu
145                 150                 155                 160

Leu Phe Gly Thr Ile Asp Thr Trp Leu Leu Trp Asn Leu Thr Gly Gly
                165                 170                 175

Ala Glu Gly Asp Asn Gly Gln Pro Ala Val His Ala Thr Asp Val Thr
            180                 185                 190

Asn Ala Ser Arg Thr Leu Leu Met Asp Leu Gly Ser Leu Gln Trp Asp
        195                 200                 205

Glu Glu Leu Cys Ala Ala Leu Asp Ile Pro Met Gln Val Leu Pro Glu
    210                 215                 220

Ile Arg Pro Ser Val Gly Asn Phe Gly Gln Val Arg Ala Arg Gly Ser
225                 230                 235                 240

Leu Ala Gly Val Pro Ile Arg Ala Ile Leu Gly Asp Gln Gln Ala Ala
                245                 250                 255

Met Phe Gly Gln Ala Cys Phe Arg Pro Gly Asp Ala Lys Cys Thr Tyr
            260                 265                 270

Gly Thr Gly Leu Phe Leu Leu Glu Asn Thr Gly Lys Thr Pro Lys His
        275                 280                 285

Ser Glu Asn Gly Leu Leu Thr Thr Val Cys Phe Gln Leu Glu Gly Glu
    290                 295                 300

Lys Pro Val Tyr Ala Leu Glu Gly Ser Val Ala Met Gly Gly Ser Leu
305                 310                 315                 320

Val Gln Trp Leu Arg Asp Asn Leu Gln Ile Ile Pro Asn Ser Pro Ala
                325                 330                 335

Ile Glu Asn Leu Ala Arg Glu Val Pro Asp Asn Gly Val Tyr Ile
            340                 345                 350

Val Pro Ala Phe Ser Gly Leu Phe Ala Pro Arg Trp Arg Pro Asp Ala
        355                 360                 365

Arg Gly Val Ile Val Gly Leu Thr Arg Phe Ala Asn Arg Lys His Leu
    370                 375                 380

```
Ala Arg Ala Val Leu Glu Ala Thr Ala Tyr Gln Val Arg Glu Val Ile
385                 390                 395                 400

Asp Ala Met Val Ala Asp Ser Gly Val Glu Leu Thr Glu Met Arg Val
            405                 410                 415

Asp Gly Gly Met Val Met Asn Glu Leu Leu Met Gln Phe Gln Ala Asp
            420                 425                 430

Val Leu Arg Ser Asp Val Thr Arg Pro Lys Asn Ile Glu Thr Thr Ala
        435                 440                 445

Thr Gly Val Ala Tyr Ala Ala Gly Leu Gly Val Gly Tyr Trp Asp Ser
    450                 455                 460

Leu Asp Val Leu Arg Asn Met Asn Glu Val Asp Lys Thr Trp His Ala
465                 470                 475                 480

Lys Met Asp Ala Asp Lys Ile Asp Glu Leu Leu Ala Glu Trp Asn Lys
                485                 490                 495

Ala Val Glu Arg Thr Tyr Asn Trp Glu Asn
            500                 505

<210> SEQ ID NO 7
<211> LENGTH: 28
<212> TYPE: DNA
<213> ORGANISM: Artificial Sequence
<220> FEATURE:
<223> OTHER INFORMATION: primer 3

<400> SEQUENCE: 7
ggaaatctgg gccaacacgc gccaagcc                                    28

<210> SEQ ID NO 8
<211> LENGTH: 28
<212> TYPE: DNA
<213> ORGANISM: Artificial Sequence
<220> FEATURE:
<223> OTHER INFORMATION: primer 4

<400> SEQUENCE: 8
ggcttggcgc gtgttggccc agatttcc                                    28

<210> SEQ ID NO 9
<211> LENGTH: 4261
<212> TYPE: DNA
<213> ORGANISM: Artificial Sequence
<220> FEATURE:
<223> OTHER INFORMATION: DNA sequence of glpDFK-2 from pECCG117-cdi
      glpDFK-2

<400> SEQUENCE: 9
gctgtgtggc gtatgtcgcg cagcccgttt tttgccgcca ccaccactgg ttacatcacc    60
tgctaccagt tgttatcatc tccgaaacta aaaaacttgc tctaggggtc tagtctgcct   120
aacttacggt tcagtagggt tggggcaaac ctcggacgca agaaggagt gtggcaacta    180 tgaccacgaa atcccattgc acattcaacc ccgactacta ccaggacgtc tggcagcgct   240
tcggtgaaga gaatacgac gttgtcgtca tcggtggcgg ctccgtcggc gcaggcgcag    300
gcctcgacgc agccatccgc ggcctcaaag tggccgtcgt agagtcccga gacttcgcag    360
ccggcacctc ctcacgatca tcaaaaatgt tccacggtgg cctgcgatat ctcgccatgc    420
tggacttcaa gctagtggcc gaatccctcc acgagcgcga actcaacatg tcgacgctcg    480
caccgcacct agtcaagccg ctgaaattcc tcttccccct cacacaccac gtgtgggaac    540
gggtgatgat gttcggcggc tttactcttt acgacctcat gggcggcgca aaatcagtcc    600
ccatgcaaaa gcactactcc cgcaagggaa cactcgccat ggccccagga ctaaaagacg    660
```

```
acgctgtggt cggatccgtc cgctactttg acacgcttgt cgacgacgcc cgccacacca    720
tgacagtcct acgcaccgcc ggcgaactcg gcgcagatgt tcgcccctcc acccaagtag    780
tcggctttga aaagacggc caacgcgtgg tcggcgccat cctccaagac accgacaccg     840
gcgaacaaac caccatccgc ggcaaggtat tcatcaacgc caccggcgta tggaacgacc    900
acattgaaaa gctcgccggc ggcaacggcc ccttctcggt ccacgcctcc aagggcgtac    960
acatcgtggt accaaagaac gtctttgatg ccgacgcagc catgtgcttt gtcaccgaaa   1020
agtccgtgct cttcgtgatc ccatggggtg aatactggat catcggcacc accgacaccg   1080
actgggatct caaccgcgca gaccccgcac caactgccgc cgacatcaac tacatcctcg   1140
acgaagtcaa ccagcgagtc cgccggccca tccaacactc cgacatcgtc ggcgtgtact   1200
ccggactccg cccgctgctc tccggcaaat ccgacaccac caccaagctg tcgcgcaacc   1260
acgccgtagc aaaggtcatg cctggactcg tctccgtcgc cggcggtaag tacaccacct   1320
accgtgtgat cggcaaggat gcagtcgacc tcgccaccga agacttggac ttccgcgtac   1380
cagcctccga atcggaacgc accccgatcc tcggtgccga cggctaccac gccctacaaa   1440
accaagcacc acgcatcgcc cgcaccttcg gcaccacaga ggacgtcgtc gagcacctgc   1500
tcggccgcta cggctccctc gtccatgagg tcctagaacc gagcgtcgat aaacctgagc   1560
tgctcgaacc catcccaggc gcgccgggct acattaaggc agaggccgtc tatgccgtca   1620
cccacgaggg tgccctgcac gtcgaggaca tcgtggaacg tcgcctacgt gccggcatcg   1680
aatacgccga ccgtggcgtt gccgcagctc ccgccatcgc cgagctcgtt gccgactacc   1740
ttggctggga cgccgagcgc accgccgccg aggtcaccgc gttcaccgac cgcgtgtccg   1800
ccgaaatcgc cgccgagaag gagctcactg acaaagccgc caacgagcac atcgtggcag   1860
gctccgcggt gcgcagctat gtggatgtgt caggtgataa ctaatgaccg ccctacaagc   1920
attcggctgg gagttttggg gcacagccct cctgcttctc ctcggtaacg gcgtttgcgc   1980
cgtcaacagc ctgcgcacct ccgcaggcaa aggcactggc tgggtgctta tcgctttcgg   2040
ctggggcatg gcgtattcg tcggtgcctc agtggcaagc cccagcggcg ccacctcaa    2100
cccagcggtc actatcgcgc tggcgatcaa aggcagcaca ccatggaacc tggtaggcgg   2160
ctatgttctc gggcagttcc tcggagccat gtttggtgca atcctgtgct ggctgacatt   2220
caagcagctt ttcgacgcca acaaccgga cgaaaacgga acgtcacgg gagctaaccg     2280
caccaccggc ggtatcttct tcaccggccc cgcccacaat cagaacgggt ggaacatggt   2340
caccgagttc atcggcacct gcgtactgct gctgttcatc ttcttcggcc ccaccggcgg   2400
cgacctaggc cccatgacct atttcgcagt cgcctttgtg atcgttgcca taggcttgtc   2460
gctaggcaca ccgaccggct acgccatcaa ccctgtgcgt gacctcggcc ccgcctgat   2520
gtacgccttc gtgctgccca ttaaagacaa aggatccgcg aactgggct atgcctgggt    2580
tccgatcgtc ggccccatga tcgccgcggt cttctgcgga gtgctggcca ctgtagtgct   2640
gtagtgaaag ggaaccacac caatgaatca accacagtat gttgctgcga ttgaccaagg   2700
aacgacgtcg acacgctgca tcattttcga ccacaacggc caacaagtag gcgttggcca   2760
gtacgaacac gaacaaatct tcccccaaaa aggctgggta gagcacaacc caatggaaat   2820
ctgggccaac acgcgccaag ccgttgggac agcactcgcc gaaagcgacg tctcccgtga   2880
agacatcgta gccgtaggca taacaaacca gcgtgaaacc acggtggtct ggaacaaaac   2940
tactggtgaa cccatatata acgccattgt gtggcaggac acccgcacta actccatctg   3000
ctcggagtta gcccaaggcg accctgcccg gtggcagaaa cgtaccggtt tgctcatcaa   3060
```

```
ctcataccoc gcgggccccc gactcaagtg gatattggac aacgtcgagg gtgcccgcga    3120
actagcagag aacggcgatt tgctcttcgg aaccattgat acgtggttgc tgtggaacct    3180
gaccggcggt gccgagggtg acaacggcca gcctgccgtt cacgctaccg acgtaaccaa    3240
tgcctcccgc accctactca tggatctgga atccctgcaa tgggatgagg aactatgtgc    3300
cgcgttggat attccaatgc aggtgttgcc agagattcgt ccttcagttg gtaacttcgg    3360
ccaagtacgt gcacgtggat cactagctgg tgttccgatc cgcgccatcc tcggtgacca    3420
gcaagccgca atgttcggac aggcatgctt ccggccaggt gatgccaaat gtacatacgg    3480
cacggggttg ttccttctgg agaacacagg caaaaccccg aagcattccg aaaacggttt    3540
gctcaccacc gtgtgtttcc agctcgaagg cgaaaaaccg gtctatgccc tcgaaggatc    3600
cgttgccatg gggggctcgc tcgtccaatg gctacgcgaa aaccttcaaa tcatcccgaa    3660
ctcgcccgcc attgaaaacc tcgcacgcga agtaccgac aacggtggcg tgtacatcgt    3720
ccccgcattc tccggactat tcgcaccacg ctggcgcccc gacgcccgcg ggtcatcgt    3780
gggcctgacc cgctttgcca accgcaagca cctcgcccgc gcagtactcg aggccaccgc    3840
ctaccaagtg cgcgaagtga tcgatgccat ggtcgcggat tccggagtag aactcaccga    3900
aatgcgtgtc gacggcggca tggtcatgaa cgaactgctc atgcaattcc aagccgacgt    3960
cctacgatcc gacgtcacgc gccccaagaa catcgagacc acagccaccg gcgtagccta    4020
cgcagccggc ctcggcgtgg gctactggga cagcctcgac gtactccgca acatgaacga    4080
agtggacaaa acctggcacg ccaagatgga cgccgacaag atcgacgagc tccttgccga    4140
atggaacaaa gcagtcgaac gcacctacaa ctgggaaaac taactgcctc ctgaaataac    4200
agcaaacccg acgaactatc cagctcgtcg ggtttgtttt gtgggggttgg gtttgatgat    4260
t                                                                   4261
```

<210> SEQ ID NO 10
<211> LENGTH: 506
<212> TYPE: PRT
<213> ORGANISM: Artificial Sequence
<220> FEATURE:
<223> OTHER INFORMATION: Amino acid sequence of GlpK from pECCG117-cdi
      glpDFK-2

<400> SEQUENCE: 10

```
Met Asn Gln Pro Gln Tyr Val Ala Ala Ile Asp Gln Gly Thr Thr Ser
  1               5                  10                  15

Thr Arg Cys Ile Ile Phe Asp His Asn Gly Gln Val Gly Val Gly
             20                  25                  30

Gln Tyr Glu His Glu Gln Ile Phe Pro Gln Lys Gly Trp Val Glu His
         35                  40                  45

Asn Pro Met Glu Ile Trp Ala Asn Thr Arg Gln Ala Val Gly Thr Ala
     50                  55                  60

Leu Ala Glu Ser Asp Val Ser Arg Glu Asp Ile Val Ala Val Gly Ile
 65                  70                  75                  80

Thr Asn Gln Arg Glu Thr Thr Val Val Trp Asn Lys Thr Thr Gly Glu
                 85                  90                  95

Pro Ile Tyr Asn Ala Ile Val Trp Gln Asp Thr Arg Thr Asn Ser Ile
            100                 105                 110

Cys Ser Glu Leu Ala Gln Gly Asp Pro Ala Arg Trp Gln Lys Arg Thr
        115                 120                 125

Gly Leu Leu Ile Asn Ser Tyr Pro Ala Gly Pro Arg Leu Lys Trp Ile
    130                 135                 140
```

```
Leu Asp Asn Val Glu Gly Ala Arg Glu Leu Ala Glu Asn Gly Asp Leu
145                 150                 155                 160

Leu Phe Gly Thr Ile Asp Thr Trp Leu Leu Trp Asn Leu Thr Gly Gly
                165                 170                 175

Ala Glu Gly Asp Asn Gly Gln Pro Ala Val His Ala Thr Asp Val Thr
                180                 185                 190

Asn Ala Ser Arg Thr Leu Leu Met Asp Leu Glu Ser Leu Gln Trp Asp
            195                 200                 205

Glu Glu Leu Cys Ala Ala Leu Asp Ile Pro Met Gln Val Leu Pro Glu
            210                 215                 220

Ile Arg Pro Ser Val Gly Asn Phe Gly Gln Val Arg Ala Arg Gly Ser
225                 230                 235                 240

Leu Ala Gly Val Pro Ile Arg Ala Ile Leu Gly Asp Gln Gln Ala Ala
                245                 250                 255

Met Phe Gly Gln Ala Cys Phe Arg Pro Gly Asp Ala Lys Cys Thr Tyr
                260                 265                 270

Gly Thr Gly Leu Phe Leu Leu Glu Asn Thr Gly Lys Thr Pro Lys His
            275                 280                 285

Ser Glu Asn Gly Leu Leu Thr Thr Val Cys Phe Gln Leu Glu Gly Glu
            290                 295                 300

Lys Pro Val Tyr Ala Leu Glu Gly Ser Val Ala Met Gly Gly Ser Leu
305                 310                 315                 320

Val Gln Trp Leu Arg Asp Asn Leu Gln Ile Ile Pro Asn Ser Pro Ala
                325                 330                 335

Ile Glu Asn Leu Ala Arg Glu Val Pro Asp Asn Gly Gly Val Tyr Ile
                340                 345                 350

Val Pro Ala Phe Ser Gly Leu Phe Ala Pro Arg Trp Arg Pro Asp Ala
            355                 360                 365

Arg Gly Val Ile Val Gly Leu Thr Arg Phe Ala Asn Arg Lys His Leu
            370                 375                 380

Ala Arg Ala Val Leu Glu Ala Thr Ala Tyr Gln Val Arg Glu Val Ile
385                 390                 395                 400

Asp Ala Met Val Ala Asp Ser Gly Val Glu Leu Thr Glu Met Arg Val
                405                 410                 415

Asp Gly Gly Met Val Met Asn Glu Leu Leu Met Gln Phe Gln Ala Asp
            420                 425                 430

Val Leu Arg Ser Asp Val Thr Arg Pro Lys Asn Ile Glu Thr Thr Ala
            435                 440                 445

Thr Gly Val Ala Tyr Ala Ala Gly Leu Gly Val Gly Tyr Trp Asp Ser
450                 455                 460

Leu Asp Val Leu Arg Asn Met Asn Glu Val Asp Lys Thr Trp His Ala
465                 470                 475                 480

Lys Met Asp Ala Asp Lys Ile Asp Glu Leu Leu Ala Glu Trp Asn Lys
                485                 490                 495

Ala Val Glu Arg Thr Tyr Asn Trp Glu Asn
                500                 505
```

PROCESS FOR PRODUCING FERMENTATION PRODUCT FROM CARBON SOURCES CONTAINING GLYCEROL USING CORYNEBACTERIA

RELATED APPLICATIONS

This application is a 35 U.S.C. §371 national phase application of PCT/KR2008/000391 (WO 2008/091093), filed on Jan. 22, 2008, entitled "Process For Producing Fermentation Product From Carbon Sources Containing Glycerol Using Corynebacteria," which application claims the benefit of Korean Patent Application Serial No. 10-2007-0007513, filed on Jan. 24, 2007. Each of these applications is specifically incorporated herein by reference in its entirety.

TECHNICAL FIELD

The present invention relates to a method for producing fermentation product from various carbon sources containing glycerol using Corynebacteria. More particularly, the present invention relates to a method for producing fermentation product such as amino acid using glycerol with high yield and high productivity, by fermenting Corynebacteria introduced with a foreign gene in relation to utilizing foreign glycerol capable of accumulating commercially useful amino acids such as aspartate, threonine, lysine, methionine, isoleucine, asparagine, glutamic acid, glutamine, proline, alanine, valine, leucine, tryptophan, tyrosine, phenylalanine and their metabolic intermediates in the culture medium supplemented with glycerol, the byproduct generated during the production of BioDiesel in oil industry, as a carbon source.

BACKGROUND ART

The mentioned amino acids are very useful. Aspartate has been used as a raw material of aspartame, and lysine, threonine, methionine and tryptophan have been used as amino acids for feeds, foods and medicines. Asparagine, isoleucine, glutamic acid, glutamine, leucine, valine, alanine, proline, phenylalanine and tyrosine have been used as amino acids for foods and medicines. Also, homoserine and O-succinylhomoserine can be used as a precursors of amino acids production.

According to the continuous increase of oil price, development of an alternative energy using a recycling materials in nature is getting attention. Among many candidates for alternative energy source, BioDiesel obtained from plant oil and Bioethanol produced by fermentation are the most attractive candidates. BioDiesel indicates fatty acid methyl ester or fatty acid ethyl ester synthesized by esterification of methanol produced using plant oil as a substrate in the presence of a catalyst. During the synthesis, the byproduct, glycerol, is necessarily generated by 10% of the total weight.

Glycerol ($C_3H_8O_3$) is converted from glucose ($C_6H_{12}O_6$) by 1 step reduction, which can provide improved reducing power during the metabolism of a microorganism. Many products produced by fermentation require reducing power in their metabolic pathways. Therefore, if the glycerol could be effectively used as a substrate, the yield and productivity of the desired fermentation product would be improved. Despite the expectation, the studies on glycerol have been limited to reuterin (Talarico et. al., Antimicrob. Agents Chemother., 32:1854-1858 (1988)), 2,3-butanediol (Biebl, et al., Appl Microbiol. Biotechnol. 50:24-29 (1998)), 1,3-propanediol (Menzel, et. al., Enzyme Microb. Technol., 20:82-86 (1997)), succinic acid (Korean Patent No. 10-0313134), itaconic acid (U.S. Pat. No. 5,457,040), 3-hydroxypropanaldehyde (Doleyres et al. Appl. Microbiol. Biotechnol. 68(4):467-474 (2005)) and propionic acid (Himmi et al., Appl. Microbiol. Biotechnol., 53: 435-440 (2000)). That is because the price of glycerol is higher than that of any other carbon sources used for the fermentation in this industry. Now, studies to produce glycerol by fermentation are undergoing (Wang et al., Biotechnol. Adv., 19(3):201-223 (2001)).

However, with the increase of BioDiesel production, glycerol production is also increasing, resulting in the rapid reduction of the price. Accordingly, there has been a report that 1,3-propandiol (Gonzalez-Pajuelo et al., J. Ind. Microbiol. Biotechnol. 31: 442-446, (2004)), hydrogen and ethanol (Ito et al., J. Biosci. Bioeng., 100(3): 260-265 (2005)) have been produced by using the byproduct of BioDiesel including glycerol. However, no reports have been made to produce the most representative fermentation product, amino acids, and other major metabolites by using glycerol.

Glycerol has been produced so far in the industry of soap, fatty acid, wax and surfactants. However, as mentioned above, the problem to effectively treat byproduct including glycerol according to increase of BioDiesel production may occur. In the meantime, the price of the purified glycerol is also expected to be dropped. Therefore, the production of useful fermentation products using glycerol might bring effects more than expected.

The cases of using glycerol in microorganisms have been reported in *E. coli* and *Klebsiella pneumoniae*. In *E. coli*, extracellular glycerol infiltrates in cells by using GlpF, one of aquaglyceroporin having permeability for water, glycerol and urea, without energy consumption (Heller et al., J. Bacteriol. 144:274-278, (1980)). The glycerol is converted into glycerol-3-phosphate by glycerol kinase, which is converted again into dihydroxyacetone phosphate (DHAP) by glycerol-3-phosphate dehydrogenase and then converted into glyceroaldehyde-3-phosphate (G-3-P) by triosephosphate isomerase (TpiA), followed by final metabolism. (Lin E C, Annu. Rev. Microbiol. 30:535-578, (1976)). In the case that glycerol kinase has no activity, glycerol is converted into dihydroxyacetone (DHA) by glycerol dehydrogenase (Gdh), which is converted again into dihydroxyacetone phosphate (DHAP) by glycerol kinase or dihydroxyacetone kinase (DHA kinase), followed by conversion again into glyceraldehydes-3-phosphate (G-3-P) before final metabolism (Paulsen et al., Microbiology, 146:2343-2344, (2000)). Such glycerol metabolic pathway is regulated by various factors. Particularly, when glycerol and glucose are together, the wild type *E. coli* uses glucose first, exclusively, and then uses glycerol (Lin, Annu. Rev. Microbiol. 30:535-578, (1976)).

Microorganisms of *Corynebacterium* genus are the ones that have been widely used in industrial fields. For example, *Corynebacterium glutamicum* has been used for the production of such amino acids as lysine and monosodium glutamate, and *C. ammoniagenes* has been widely used for the production of nucleic acid by fermentation industrially. It has reported that Corynebacteria can use various carbon sources such as glucose and raw sugar for fermentation. It has also been reported that Corynebacteria can use xylose by the introduction of a gene such as xylAB (Kawaguchi et al., Appl. Envion. Microbiol. 72(5): 3418-3428 (2006)). However, there are rare cases reporting that Corynebacteria use glycerol as a carbon source. The case of using glycerol in *Corynebacterium glutamicum* are also very low (Korean Patent Application No. 2006-057633).

Among the microorganisms of *Corynebacterium* genus, only 4 microorganisms were analyzed to identify their total genome sequences. And, a complete gene using glycerol was found only in *Corynebacterium diphtheriae* and such genes involved in glycerol consumption as GlpF was deficient in other three microorganisms, *Corynebacterium glutamicum*, *Corynebacterium efficiens*, and *Corynebacterium jeikeium*. The deficiency of the gene is the major obstacle for Corynebacteria to use glycerol efficiently.

DISCLOSURE OF INVENTION

Technical Problem

As explained hereinbefore, there is value-added by using glycerol which is the byproduct of BioDiesel production as a carbon source. Thus, based on that, the present inventors focused our studies on the glycerol availability of Corynebacteria with industrially high utility value such as *Corynebacterium glutamicum* and *Corynebacterium ammoniagenes*. As a result, the present inventors completed this invention by confirming that the glycerol availability could be remarkably improved by introducing a foreign gene involved in the use of glycerol into those Corynebacteria.

It is an object of the present invention to provide a gene involved in the use of glycerol to improve glycerol assimilation of Corynebacteria significantly.

It is another object of the present invention to provide a mutant originated from Corynebacteria using glycerol either alone as a carbon source or together with other carbon sources.

It is further object of the present invention to provide a method for producing fermentation product by fermenting Corynebacteria using a carbon source comprising glycerol or a part of glycerol.

Technical Solution

The above objects and other objects of the present invention can be achieved by the following embodiments of the present invention.

The present invention is described in detail hereinafter.

To achieve the object of the invention, the present invention provides a gene involved in the use of glycerol to improve glycerol assimilation of Corynebacteria significantly.

The gene involved in the use of glycerol herein indicates a gene encoding glycerol uptake facilitator protein originated from *Corynebacterium diphtheriae* (referred as glpF hereinafter), a gene encoding glycerol kinase which is the enzyme producing glycerol-3-phosphate by phosphorylation using ATP (referred as glpK hereinafter), and a gene encoding glycerol-3-phospho dihydrogenase which is the enzyme producing dihydroxyacetone-3-phosphate by oxidizing glycerol-3-phosphate (referred as glpD hereinafter).

The gene includes any gene encoding a polypeptide in Corynebacteria that plays a role in uptake of extracellular glycerol and converting the glycerol into glycerol-3-phosphate by phosphorylation, and converting glycerol-3-phosphate into dihydroxyacetone-3-phosphate, and then finally converting dihydroxyacetone-3-phosphate into glyceraldehyde-3-phosphate, the intermediate of glycolysis, to metabolize glycerol.

The gene can be originated from animals, plants, and microorganisms. It is more preferred to select a gene originated from a microorganism, particularly from *Corynebacterium diphtheriae* NCTC13129 (Gene Bank Accession No: NC_002935).

The present invention also provides a mutant originated from Corynebacteria using glycerol either alone as a carbon source or together with other carbon sources.

The strain used in this invention can be growth consuming glycerol and glucose simultaneously to use glycerol effectively. When glucose and glycerol are given simultaneously as a carbon source, the wild type *E. coli* uses glucose exclusively, and after consuming all the glucose the wild type *E. coli* uses glycerol, which is so called 'diauxy'. Thus, when a complex carbon source containing glycerol is supplied, fermentation efficiency is reduced.

To overcome the above problem, the present inventors investigated the possibility of simultaneous using of glucose and glycerol in the strain. And as a result, the inventors confirmed that glycerol and other carbon sources could be effectively used by the insertion of a foreign gene involved in the use of glycerol originated from Corynebacteria.

In a preferred embodiment of the present invention, the present inventors provide a microorganism containing the gene encoding GlpF (Gene Bank Accession No: NC_940539.1), GlpK (Gene bank Accession No: NC_940538.1) and GlpD (Gene Bank Accession No: NC_040540.1), the protein involved in the use of glycerol, originated from *Corynebacterium diphtheriae*. The transformation of Corynebacteria with the gene can be performed by the conventional method known to those in the art, and a mutant of *Corynebacterium* producing amino acids using a carbon source comprising glycerol or a part of glycerol can be provided.

The vector for the present invention is not limited to a specific one and any informed expression vector can be used. Particularly, *E. coli-Corynebacterium* shuttle vector pECCG117 (Biotechnology letters vol 13, No. 10, p. 721-726 (1991)) is preferred.

In this description, the term 'transformation' indicates the process of introducing a gene into a host cell and expressing the gene therein. The transformed gene includes any gene, either inserted into chromosome of the host cell or presented in the outside of chromosome as long as it can be expressed in the cell. The gene is a polynucleotide capable of encoding a polypeptide and containing DNA and RNA. The gene is not limited in its form for introduction, as long as it can be expressed in the host cell. For example, the gene can be introduced into the host cell as an expression cassette, the polynucleotide construct that contains every necessary element for auto-expression. The expression cassette comprising a promoter operably linked to the gene, a transcription terminator, a ribosome binding site, and a translation terminator. The expression cassette can be the expression vector capable of auto-replication. Also, the gene can be operably linked to the sequence necessary for the expression in the host cell by introducing into a host cell as in itself or the form of a polynucleotide construct.

In a preferred embodiment of the present invention, the transformation is performed by transforming a host cell with the vector containing glpDFK gene and introducing the obtained plasmid by electric pulse method. The transformed host cell can be *E. coli* CO02-0014 (Accession No: KCCM 10834P).

In this invention, the microorganism transformed with a gene involved in the use of glycerol to produce amino acids effectively using glycerol can be one of Corynebacteriaceae, more preferably a microorganism of *Corynebacterium* genus, and most preferably a microorganism selected from the group consisting of *Corynebacterium glutamicum* (ex. ATCC13032), *Corynebacterium ammoniagenes* (ex. ATCC 6872), *Brevibacterium lactofermentum* (ex. ATCC13869), *Brevibacterium flavum* (ex. ATCC14067), *Corynebacterium thermoaminogenes* (ex. FERM-BP1539) and *Corynebacterium efficiens* (ex. *C. efficiens* str. YS-314), but not always limited thereto. And also, the microorganism producing useful materials such as amino acids or nucleic acids, for example *Corynebacterium glutamicum* SM5 producing glutamic acid and *Corynebacterium glutamicum* CF 905 (KFCC-10881) producing lysine, can be included, but not always limited thereto.

The present invention further provides a method for producing fermentation product by fermenting Corynebacteria using a carbon source comprising glycerol or a part of glycerol. Particularly, the present invention provides a method for producing fermentation product using glycerol comprising the steps of: transforming a host cell with the vector containing glpDFK which is a gene complex facilitating the use of glycerol; transforming Corynebacteria with the plasmid obtained from the transformed host cell by electric pulse method; culturing the transformed Corynebacteria by inoculating in the culture medium containing glycerol or a part of glycerol as a carbon source; and separating fermentation product from the culture medium.

In the method for producing fermentation product of the present invention, culture of the microorganism can be performed in a proper medium and under proper culture conditions known to those in the art. These conditions can be regulated by those in the art according to the selected strain. The cultivation methods are exemplified by batch, continuous and fed-batch cultures, but not always limited thereto. Various culture methods are described in "Biochemical Engineering" by James M. Lee, Prentice-Hall International Editions, pp 138-176.

The medium has to meet the requirements for the culture of a specific strain. The medium used in this invention contains glycerol or a part of glycerol as a carbon source, preferably contains glycerol by 1 g-300 g per 1 liter of culture medium. In addition to glycerol, other carbon sources can be properly added, and at this time glucose is preferred as a carbon source. As a nitrogen source, such organic nitrogen source as peptone, yeast extract, gravy, malt extract, corn steep liquor and soybean flour, and such inorganic nitrogen source as urea, ammonium sulfate, ammonium chloride, ammonium phosphate, ammonium carbonate and ammonium nitrate can be included in the medium. As a phosphate source, potassium dihydrogen phosphate, dipotassium hydrogen phosphate and their corresponding sodium-containing salts can be included in the medium. Besides, a metal salt such as magnesium sulfate or iron sulfate can also be included. Amino acids, vitamins and proper precursors can be included as well. These medium or precursors can be added to the culture by batch-type or continuously.

pH of the culture can be adjusted during the cultivation by adding such a compound as ammonium hydroxide, potassium hydroxide, ammonia, phosphoric acid and sulfuric acid. The generation of air bubbles can be inhibited during the cultivation by using an antifoaming agent such as fatty acid polyglycol ester. To maintain aerobic condition of the culture, oxygen or oxygen-containing gas can be injected into the culture. The temperature of the culture is preferably 20-45° C., more preferably 25-40° C. The cultivation can be continued until the production of amino acid reaches a desired level, and the preferable culture time is 10-160 hours.

BRIEF DESCRIPTION OF THE DRAWINGS

The application of the preferred embodiments of the present invention is best understood with reference to the accompanying drawings, wherein.

ATCC13032: *Corynebacterium glutamicum* ATCC13032

DFK-1: *Corynebacterium glutamicum* ATCC13032/pECCG117-cdi glpDFK-1

DFK-2: *Corynebacterium glutamicum* ATCC13032/pECCG117-cdi glpDFK-2

BEST MODE FOR CARRYING OUT THE INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLES

Example 1

Screening and Cloning of a Gene Involved in the Use of Glycerol which is Operable in Corynebacteria The nucleotide sequence of the gene involved in the use of glycerol of *Corynebacterium diphtheriae* has already been identified and officially released. Information about genes encoding GlpF, GlpK and GlpD (glpF, glpK and glpD respectively) which are proteins of *Corynebacterium diphtheriae* associated with the use of glycerol and adjacent nucleotide sequences was obtained from GeneBank, NIH, USA. Gene Bank Accession No. of GlpF of *Corynebacterium diphtheriae* was NC_940539.1, Gene Bank Accession No. of GlpK was NC_940538.1, and the Gene Bank Accession No. of GlpD was NC_940540.1. The genes were confirmed to be arranged in a series on a genome. So, one time PCR could amplify all of the three genes as a single polynucleotide. Primers represented by SEQ. ID. NO: 1 and NO: 2 were used for PCR to amplify the genes involved in the use of glycerol of *Corynebacterium diphtheriae*.

```
SEQ. ID. NO: 1:
5' GATGCGGCCGCGCTGTGTGGCGTATGTCG 3'

SEQ. ID. NO: 2:
5' GATGCGGCCGCAATCATCAAACCCAACCCCA 3'
```

Chromosome of *Corynebacterium diphtheriae* NCTC13129 was purchased from American Type Culture Collection (ATCC) (ATCC ID. No: 700971D-5) to amplify the gene involved in the use of glycerol of *Corynebacterium diphtheriae*. PCR was performed using the chromosome of *Corynebacterium diphtheriae* NCTC13129 as a template to amplify the gene involved in the use of glycerol. PCR was performed as follows; predenaturation at 94° C. for 3 minutes, denaturation at 94° C. for 30 seconds, annealing at 56° C. for 30 seconds, polymerization at 72° C. for 4 minutes 30 seconds, 25 cycles from denaturation to polymerization, and final extension at 72° C. for 5 minutes. As a result, 4281 bp sized polynucleotide was obtained. The polynucleotide was cloned into pCR2.1 by using TOPO TA cloning kit (Invitrogen).

Example 2

Determination of Nucleotide Sequence and Restoration of Amino Acids Mutation of the glpDFK Gene The plasmid obtained above was digested with Not I to obtain a DNA fragment containing the gene involved in the use of glycerol. The DNA fragment was cloned into pECCG117, E. coli-Corynebacterium shuttle vector, followed by transformation of E. coli TOP10. The transformed strain was name "E. coli CO02-0014" which was deposited at KCCM (Korean Culture Center of Microorganisms) of KFCC (Korean Federation of Culture Collection), the International Depository Authority located at 361-221, Hongje-1-Dong, Seodaemungu-Gu, Seoul, Korea, on Jan. 8, 2007 (Accession No: KCCM 10834P).

The plasmid obtained by the conventional plasmid miniprep was named pECCG117-cdi glpDFK-1. DNA nucleotide sequence of the pECCG117-cdi glpDFK-1 was determined and accordingly it was confirmed that the nucleotide sequence from $171^{st}$ to $1904^{th}$ encoded glpD gene (SEQ. ID. NO: 4), the nucleotide sequence from $1904^{th}$ to $2644^{th}$ encoded glpF gene (SEQ. ID. NO: 5) and the nucleotide sequence from $2663^{rd}$ to $4181^{st}$ encoded glpK gene (SEQ. ID. NO: 6) and there were 5 nucleotide sequence changes (SEQ. ID. NO: 3), compared with the sequence obtained by the conventional genome sequencing. The changes in the nucleotide sequence was as follows; the $54^{th}$ thymine was changed into cytidine, $1598^{th}$ adenine was changed into guanine, $2608^{th}$ adenine was changed into guanine, $2829^{th}$ adenine was changed into guanine, and $3037^{th}$ adenine was changed into guanine. Among these changes, the change of the $2829^{th}$ only induced mutation of the amino acid and the rest 4 changes of the nucleotide sequence were confirmed to be silent mutation. The mutation of the amino acid was that the 56th asparagine of glpK region was changed into serine. The amino acid sequence of glpK having the mutated amino acid is represented by SEQ. ID. NO: 6.

To restore the mutated amino acid to the original asparagine, site-directed mutagenesis was performed. The primers for the site-directed mutagenesis to change the $56^{th}$ amino acid, the mutated serine into asparagine, were constructed and represented by SEQ. ID. NO: 7 and NO: 8.

SEQ. ID. NO: 7: 5' GGAAATCTGGGCCAACACGCGCCAAGCC 3'

SEQ. ID. NO: 8: 5' GGCTTGGCGCGTGTTGGCCCAGATTTCC 3'

Site-directed mutagenesis was performed with the primers above using QuickChange®II XL Site-Directed Mutagenesis kit (Stratagene). The experiment was performed according to the manufacturer's instruction. Plasmid was extracted from the obtained colonies according to the conventional method, by which nucleotide sequence was determined. As a result, it was confirmed that the $2829^{th}$ adenine was changed into guanine, so that the $56^{th}$ serine of glpK region of pECCG117-cdi glpDFK-1 was changed into asparagine, suggesting that this could produce the same protein as that GlpK protein of Corynebacterium diphtheriae produced (SEQ. ID. NO: 9; SEQ. ID. NO: 10). The obtained glpDFK plasmid was named pECCG117-cdi glpDFK-2.

Example 3

Introduction into Corynebacterium glutamicum ATCC13032

The prepared pECCG117-cdi glpDFK-1 and pECCG117-cdi glpDFK-2 were introduced into Corynebacterium glutamicum ATCC13032, respectively by electric pulse method. The cells were cultured on the plate medium containing bacto-peptone 10 g/L, yeast extract 10 g/L, beef extract 5 g/L, NaCl 2.5 g/L and kanamycin 25 µg/mL. The obtained colonies proceeded to PCR cloning to select the colonies containing the plasmid comprising the gene involved in the use of glycerol. The selected strains were named respectively Corynebacterium glutamicum ATCC13032/pECCG117-cdi glpDFK-1, and Corynebacterium glutamicum ATCC13032/pECCG117-cdi glpDFK-2.

Example 4

Glycerol Availability of Corynebacterium glutamicum ATCC13032

To confirm glycerol availability of Corynebacterium glutamicum/pECCG117-cdi glpDFK-1 and Corynebacterium glutamicum/pECCG117-cdi glpDFK-2, Corynebacterium glutamicum ATCC13032 containing the above plasmid and Corynebacterium glutamicum ATCC13032 not containing the plasmid were respectively cultured in solid minimal medium. The composition for the minimal medium is as follows.

Composition of the Minimal Medium for Corynebacterium glutamicum Culture (pH 7.2):

Glycerol 10 g/L, $KH_2PO_4$ 1 g/L, $K_2HPO_4$ 2 g/L, $MgSO_4.H_2O$ 0.4 g/L, Urea 2 g/L, $(NH_4)_2SO_4$ 5 g/L, NaCl 0.5 g/L, Nicotinic acid amide 5 mg/L, Calcium pantothenate 1 mg/L, Thiamine 3 mg/L, Biotin 200 µg/L, Trace elements 1 mL, Agar 20 g/L The inoculated strain was cultured in a 30? incubator for 48 hours. As a result, the growth of Corynebacterium glutamicum introduced with pECCG117-cdi glpDF-1 or pECCG117-cdi glpDF-2 was confirmed in the minimal medium. But, the growth of the strain not introduced with the plasmid was insignificant.

The growth of the two strains in liquid minimal medium was also investigated. First, the two strains were inoculated in seed medium, followed by culture for 24 hours. The medium was eliminated by centrifugation. The remaining medium was completely eliminated by two-time dispersion in phosphate buffer (pH 7.0). The strains were inoculated in 40 mL of minimal medium, followed by culture at 30° C. for 36 hours. The growth was compared between the two strains. Minimal mediums were supplemented with different carbon sources, 12 g/L of glucose; 12 g/L of glycerol; 6 g/L of each glucose and glycerol, to compare glycerol availability. And the results are shown in FIG. 1.

Figure 1:
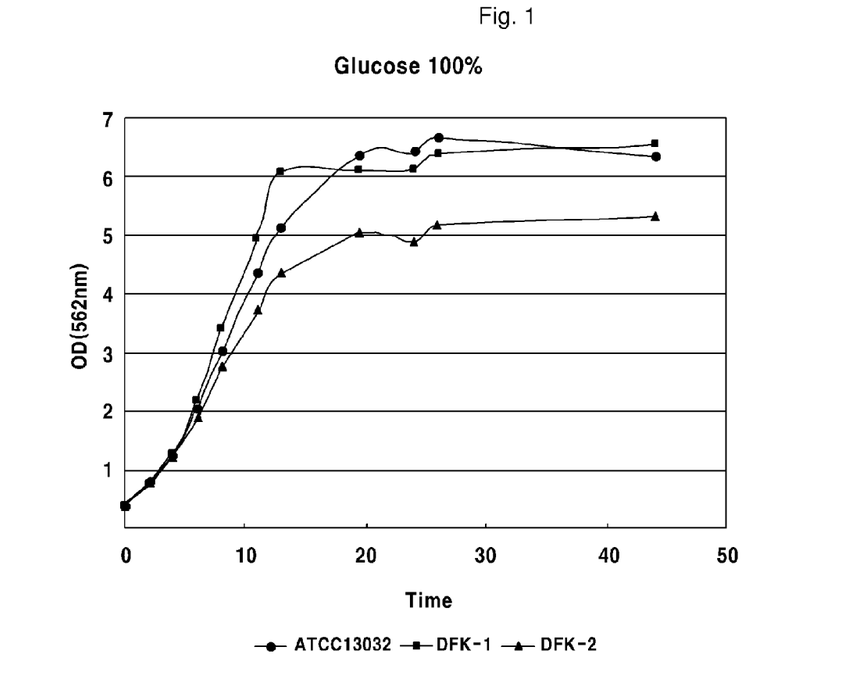
FIG. 1 illustrates the time-dependent growth rates, represented by optical densities, of *Corynebacterium glutamicum* ATCC13032, *Corynebacterium glutamicum* ATCC13032/pECCG117-cdi glpDFK-1 and *Corynebacterium glutamicum* ATCC13032/pECCG117-cdi glpDFK-2 in the minimal medium supplemented with glucose 100% as a carbon source.
Figure 2:
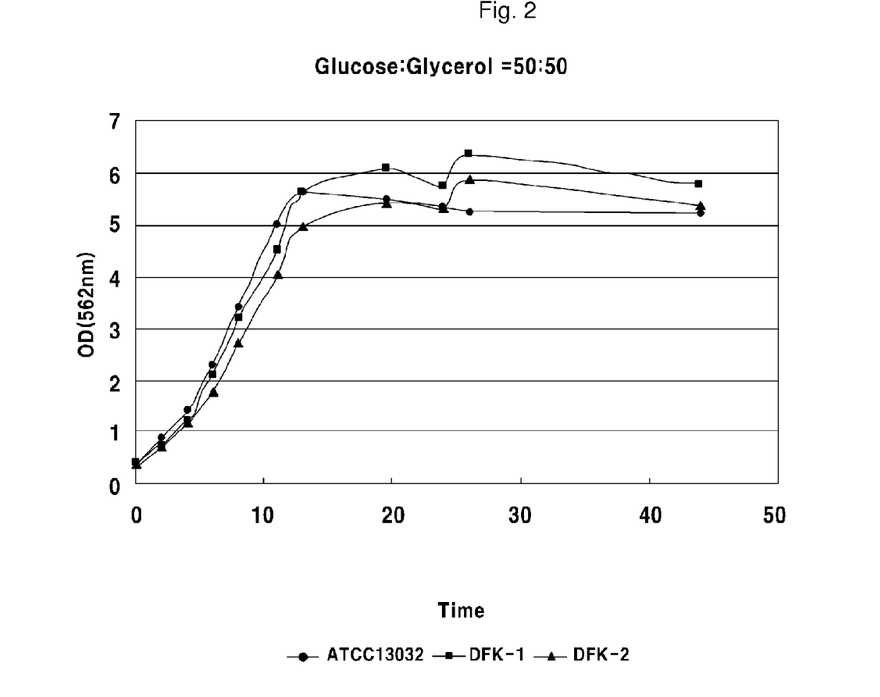
FIG. 2 illustrates the time-dependent growth rates of the microorganisms in the minimal medium supplemented with glucose:glycerol (50:50%) as a carbon source, represented by optical densities.
Figure 3:
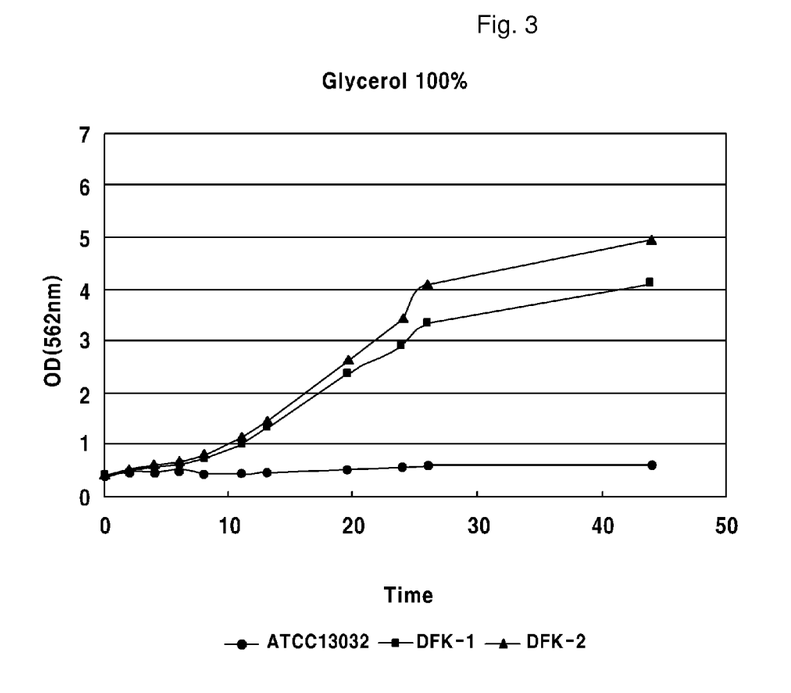
FIG. 3 illustrates the time-dependent growth rates of the microorganisms in the minimal medium supplemented with glycerol 100% as a carbon source, represented by optical densities.

As shown in FIG. 1, Corynebacterium glutamicum ATCC13032 not introduced with the gene involved in the use of glycerol was not growing so well because it could not use glycerol effectively. In the meantime, the strain introduced with the gene involved in the use of glycerol was growing well by using glycerol as a carbon source. When glycerol was added alone, it favored the growth of *Corynebacterium glutamicum* ATCC13032/pECCG117-cdi glpDFK-2. But, when glucose alone or both glucose and glycerol were added together, it favored the growth of *Corynebacterium glutamicum* ATCC13032/pECCG117-cdi glpDFK-1, so they were used in this experiment.

Example 5

Glycerol Availability of a Strain Producing Glutamic Acid

To confirm whether it was possible not only to produce useful materials but also to stimulate the growth of Corynebacteria using glycerol, the expression vector pECCG117-cdi glpDFK-1 was introduced into *Corynebacterium glutamicum* SM5 (KFCC-11112), a strain producing glutamic acid, by the same manner as described in Example 3. Glutamic acid productivity was compared between *Corynebacterium glutamicum* SM5 and *Corynebacterium glutamicum* SM5/pECCG117-cdi glpDFK-1 with different carbon sources (glycerol alone, glucose alone, and glucose and glycerol together (mixed at required ratio)). The *Corynebacterium glutamicum* SM5 and the *Corynebacterium glutamicum* SM5/pECCG117-cdi glpDFK-1 were inoculated in seed medium by one platinum loop, followed by culture at 30° C. for 18 hours. The composition of the seed medium was as follows: peptone 1 g/L, yeast extract 0.5 g/L, gravy 0.5 g/L, glucose 1 g/L, sodium chloride 0.25 g/L, urea 0.13 g/L, pH 7.2. For fermentation, 1 mL of the seed culture solution was inoculated in culture medium, followed by culture at 30° C. for 24 hours. The composition of the culture medium was as follows: HSM 3 mL, biotin 1 µg/L, waste molasses 0.05 g/L, ammonium sulfate 0.1 g/L, iron sulfate 0.002 g/L, manganese sulfate 0.002 g/L, magnesium sulfate 0.05 g/L, thiamine-HCl 500 µg/L, monopotassium phosphate 0.2 g/L, urea 0.95 g/L, pH 7.2. A carbon source was added thereto considering culture conditions. As a result, the production of L-glutamic acid was confirmed and the comparison results are shown in Table 1.

As shown in Table 1, when glycerol was used alone as a carbon source, the growth of *Corynebacterium glutamicum* SM5 was very poor and glutamic acid productivity was insignificant. In the meantime, *Corynebacterium glutamicum* SM5/pECCG117-cdi glpDFK-1 could be growing even with using glycerol alone as a carbon source, and could produce glutamic acid with similar yield, even if the productivity was reduced. When glycerol was added together with glucose (about 50:50), glutamic acid was produced without reducing yield or productivity. But, SM5 exhibited reduced glutamic aid production.

Example 6

Introduction of a Gene Involved in the Use of Glycerol into a Strain Producing Lysine and Lysine Production Using the Same To investigate whether it was possible not only to produce useful materials but also to stimulate the growth of Corynebacteria using glycerol, the expression vector pECCG117-cdi glpDFK-1 was introduced into *Corynebacterium glutamicum* CF 905 (KFCC-10881), a strain producing lysine, by the same manner as described in Example 3.

*Corynebacterium glutamicum* parent strain KFCC10881 and KFCC10881/pECCG117-cdi glpDFK-1, the strain of the present invention, were inoculated respectively in 250 ml corner-baffled flask containing 25 ml of the seed medium, followed by shaking-culture (200 rpm) at 30° C. for 20 hours. 1 ml of the seed culture solution was inoculated in 250 ml corner-baffled flask containing 24 ml of the production medium, followed by shaking-culture (200 rpm) at 30° C. for 72 hours. Upon completion of the culture, L-lysine production was measured with an amino acid analyzer. L-lysine levels in *Corynebacterium glutamicum* KFCC10881 and KFCC10881/pECCG117-cdi glpDFK-1 cultures were investigated and the results are shown in Table 2.

TABLE 1

Comparison of the growth and glutamic acid productivity in fermentation medium containing glycerol between *Corynebacterium glutamicum* SM5 and SM5/pECCG117-cdi glpDFK-1

| | | SM5 | | | | SM5/117-cdi glpDFK-1 | | | |
|---|---|---|---|---|---|---|---|---|---|
| | | 24 hr | 51 hr | 72 hr | 120 hr | 24 hr | 51 hr | 72 hr | 120 hr |
| OD | Glucose 30 g/L | 7.73 | 10.15 | 9.36 | 9.72 | 5.94 | 9.92 | 9.0 | 9.89 |
| | Glucose 15 g/L, Glycerol 15 g/L | 4.69 | 7.09 | 6.86 | 6.27 | 4.68 | 7.94 | 6.8 | 6.77 |
| | Glycerol 30 g/L | 1.45 | 2.16 | 1.56 | 1.14 | 1.87 | 1.82 | 1.4 | 1.38 |
| Consumed glucose (g/L) | Glucose 30 g/L | 10.47 | 30.93 | 30.93 | 30.93 | 8.73 | 30 | 30 | 30 |
| | Glucose 15 g/L, Glycerol 15 g/L | 5.21 | 15.21 | 15.21 | 15.21 | 3.96 | 15 | 15 | 15 |
| | Glycerol 30 g/L | 0.00 | 0 | 0.00 | 0.00 | 0.00 | 0 | 0.0 | 0.00 |
| Consumed glycerol (g/L) | Glucose 30 g/L | 0.00 | 0 | 0.00 | 0.00 | 0.00 | 0 | 0.0 | 0.00 |
| | Glucose 15 g/L, Glycerol 15 g/L | 1.46 | 2.3 | 2.30 | 2.30 | 2.15 | 15 | 15 | 15 |
| | Glycerol 30 g/L | 2.75 | 3.4 | 4.75 | 4.31 | 3.62 | 6.5 | 8.0 | 7.89 |
| Produced glutamic acid (g/L) | Glucose 30 g/L | 0.85 | 6.63 | 6.42 | 6.55 | 1.17 | 11.06 | 11.1 | 11.21 |
| | Glucose 15 g/L, Glycerol 15 g/L | 0.23 | 1.69 | 1.76 | 1.71 | 0.82 | 11.86 | 12.0 | 12.47 |
| | Glycerol 30 g/L | 0.03 | 0 | 0.05 | 0.00 | 0.19 | 1.6 | 1.9 | 1.96 |

TABLE 2

| Carbon source | | OD | Consumed Glc (g/L) | 72 h Consumed glycerol (g/L) | Lys |
|---|---|---|---|---|---|
| KFCC10881 | Glc 100 g/L | 42.4 | 100.0 | | 23.90 |
| | | 43.2 | 100.0 | | 21.74 |
| | Glc 50 g/L | 32.8 | 50.0 | 0.0 | 13.22 |
| | Glycerol 50 g/L | 32.7 | 50.0 | 0.0 | 13.52 |
| KFCC10881/ pECCG117-cdi glpDFK-1 | Glc 100 g/L | 27.4 | 100.0 | | 41.27 |
| | | 22.3 | 100.0 | | 41.42 |
| | Glc 50 g/L | 34.3 | 50.0 | 50.0 | 28.95 |
| | Glycerol 50 g/L | 33.9 | 50.0 | 50.0 | 30.89 |

As shown in Table 2, when the vector pECCG117-cdi glpDFK-1 contained gene involved in the use of glycerol was introduced into the strain producing lysine, the strain exhibited glycerol availability unlike the parent strain, and lysine production was increased.

Seed Medium (pH 7.0):

Raw sugar 20 g, Peptone 10 g, Yeast extract 5 g, Urea 1.5 g, $K_2HPO_4$ 8 g, $MgSO_4 \cdot 7H_2O$ 0.5 g, Biotin 100☐, Thiamine-HCl 1000☐, Calcium pantothenate 2000☐, Nicotinamide 2000☐ (in 1 liter of process water).

Production Medium (pH 7.0):

Glucose 100 g, $(NH_4)_2SO_4$ 40 g, Soy protein 2.5 g, Corn Steep Solids 5 g, Urea 3 g, $KH_2PO_4$ 1 g, $MgSO_4 \cdot 7H_2O$ 0.5 g, Biotin 100☐, Thiamine HCl 1000☐, Calcium-pantothenic acid 2000☐, Nicotinamide 3000☐, $CaCO_3$ 30 g (in 1 liter of process water)

INDUSTRIAL APPLICABILITY

As explained hereinbefore, the present invention provides a method for producing fermentation product with high yield using glycerol effectively which is the byproduct of oil industry and BioDiesel production. The microorganism of the present invention can produce fermentation product effectively in the medium containing a complex carbon source comprising glycerol and in the medium containing glycerol alone as a carbon source. Therefore, the microorganism capable of producing fermentation product, based on the microorganism of the present invention, can use glycerol as a carbon source effectively.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

---

The invention claimed is:

1. A method for producing a fermentation product using glycerol, comprising the following steps of:
    inoculating and culturing Corynebacteria transformed with glpDFK having the nucleotide sequence of SEQ. ID. NO: 9, the gene complex facilitating the use of glycerol in culture medium containing glycerol or a part of glycerol as a carbon source; and
    separating fermentation product from the culture.

2. The method according to claim 1, wherein the transformation is performed with the vector containing the glpDFK gene.

3. The method according to claim 1, wherein the transformation is performed by introducing a plasmid which is obtained after transforming a host cell with the vector containing the glpDFK gene, into the Corynebacteria by electric pulse method.

4. The method according to claim 3, wherein the host cell is *E. coli* CO02-0014 (Accession No: KCCM 10834P).

5. The method according to claim 1, wherein the Corynebacteria is selected from the group consisting of *Corynebacterium glutamicum*.

6. The method according to claim 1, wherein the fermentation product is glutamic acid or lysine.

* * * * *